United States Patent
Chang

(10) Patent No.: US 6,575,943 B1
(45) Date of Patent: Jun. 10, 2003

(54) PREWARNING DEVICE FOR INSTILLATION OF MEDICAL LIQUID

(76) Inventor: Hsiao-yun Emma Chang, Fl. 5, No. 102, Sec. 2, Chung Shan North Rd., Taipei (TW)

( * ) Notice: Subject to any disclaimer, the term of this patent is extended or adjusted under 35 U.S.C. 154(b) by 0 days.

(21) Appl. No.: 10/046,513

(22) Filed: Jan. 16, 2002

(51) Int. Cl.$^7$ ................................................. A61H 5/14
(52) U.S. Cl. ...................... 604/251; 604/252; 604/253; 604/254; 604/255; 604/404; 604/246
(58) Field of Search ................................. 604/251, 252, 604/253, 254, 255, 414, 404, 246

*Primary Examiner*—Manuel Mendez
*Assistant Examiner*—Kathy L. Thompson
(74) *Attorney, Agent, or Firm*—Rabin & Berdo, P.C.

(57) ABSTRACT

A prewarning device for instillation of medical liquid includes a throttling cylinder having a tubular needle connected to an open top thereof. A pointed head portion of the tubular needle is inserted into a medical liquid bottle for the medical liquid to flow into the throttling cylinder via the tubular needle. A portion of the tubular needle between the head portion and the throttling cylinder is transparent for a clamp to clamp therearound. A sensor is provided on the clamp to connect to a warning unit via a wire. The tubular needle defines a downward tapered inner space to receive a float therein. When the medical liquid bottle becomes empty, the float lowers in the tubular needle and is sensed by the sensor for the latter to actuate the warning unit to sound. The lowered float also blocks up the tubular needle to stop air from passing therethrough.

5 Claims, 6 Drawing Sheets

US 6,575,943 B1

PREWARNING DEVICE FOR INSTILLATION OF MEDICAL LIQUID

FIELD OF THE INVENTION

The present invention relates to a prewarning device for instillation of medical liquid, and more particularly to a prewarning device that buzzes and stops air from passing there through to enter a patient's vessel when a medical liquid being transfused to the patient via instillation is used up.

BACKGROUND OF THE INVENTION

It is a very common practice in a hospital to transfuse a medical liquid from a bottle into a patient's vessel via an instillation kit that usually includes a duct connected at an end to the medical liquid bottle and at another end to an injection needle. A patient's attendant family and/or a nurse has to visually check from time to time the medical liquid remained in the bottle, in order to timely replace a new bottle of medical liquid to continue the transfusion. It is, however, time and labor consuming for the patient's attendant family and the nurse to do such constant visual check of remained medical liquid being transfused via instillation.

It is therefore tried by the inventor to develop a prewarning device for instillation of medical liquid, so that the device automatically buzzes and stops air from passing therethrough to enter a patient's vessel when the medical liquid being transfused to the patient via instillation is used up.

SUMMARY OF THE INVENTION

The prewarning device for instillation of medical liquid according to the present invention mainly includes a throttling cylinder, a transparent tubular needle fixedly connected at a lower end to an open top of the throttling cylinder, a clamp provided with a sensor for clamping around a lower part of the tubular needle, and a warning unit connected to the sensor on the clamp via a wire. The tubular needle has a forward tapered head portion with a plurality of spaced slits and defines a downward tapered inner space in which a float is disposed. When the head portion of the tubular needle is inserted into a bottle containing a medical liquid to be transfused into a patient's vessel by way of instillation, the medical liquid flows from the bottle into the downward tapered inner space of the tubular needle via the slits and the float is normally located at a wider upper part of the tubular needle. When the medical liquid in the bottle is used up, the float lowers to clog a narrower lower part of the downward tapered inner space of the tubular needle. At this point, air is stopped from passing the clogged tubular needle to enter the patient's vessel, and the sensor senses the float at the lowered position and actuates the warning unit to buzz, informing the patient's attendant family or a nurse to remove the empty bottle or replace a new bottle of medical liquid.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENTS

Figure 1:
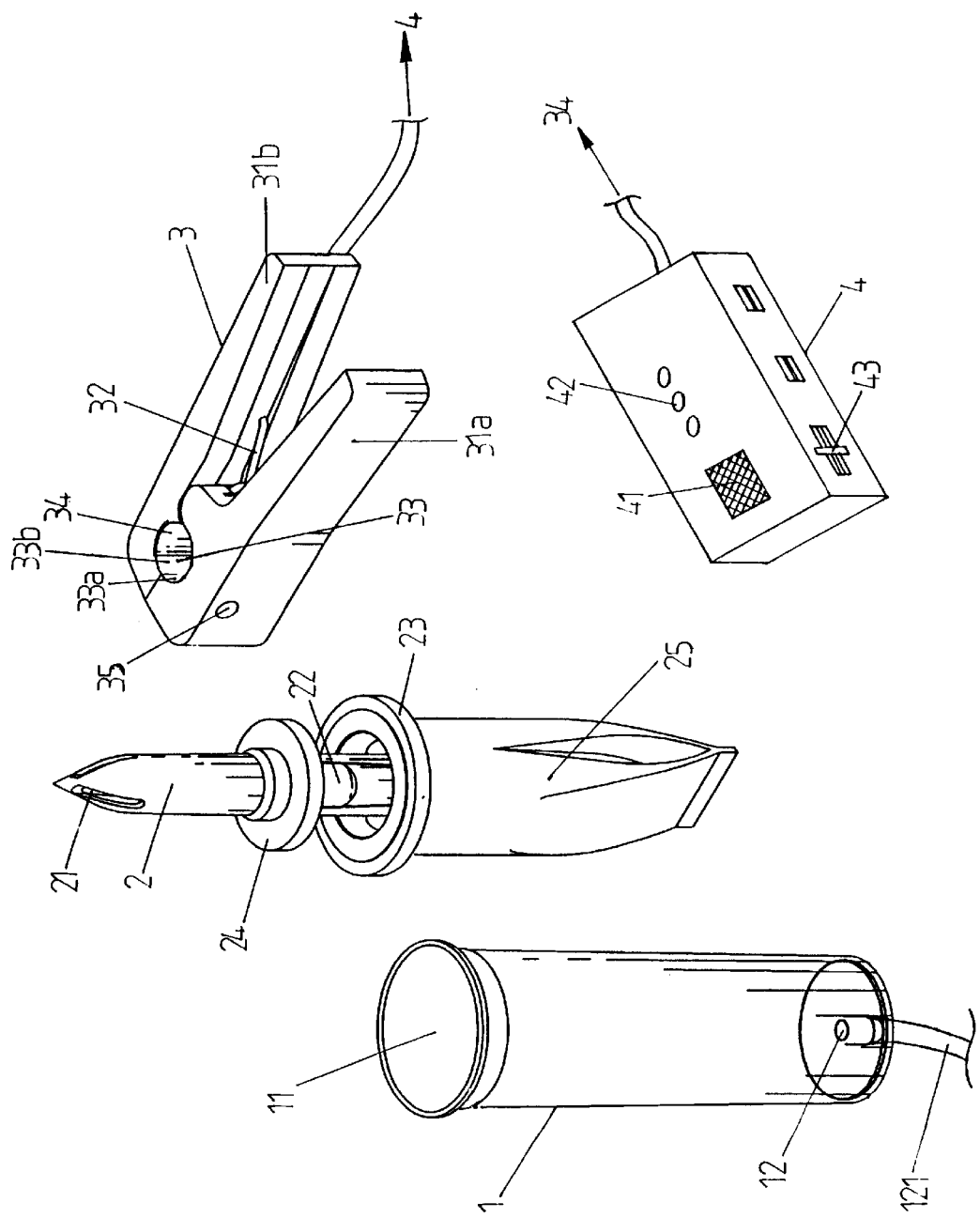
FIG. 1 is an exploded perspective view of a prewarning device for instillation of medical liquid according to the present invention.

Please refer to FIG. 1 that is an exploded perspective view of a prewarning device for instillation of medical liquid according to the present invention. As shown, the prewarning device mainly includes a throttling cylinder 1, a tubular needle 2 fixedly connected to a top of the throttling cylinder 1, a clamp 3 adapted to clamp around the tubular needle 2 at a predetermined position, and a warning unit 4 connected to the clamp 3 via a wire.

The throttling cylinder 1 is a hollow cylindrical member having an open top 11 and a closed bottom provided with a hole 12. A duct 121 is externally connected at an end to the hole 12 and at another end to a related medical instrument, such as a needle cannula.

Figure 2:
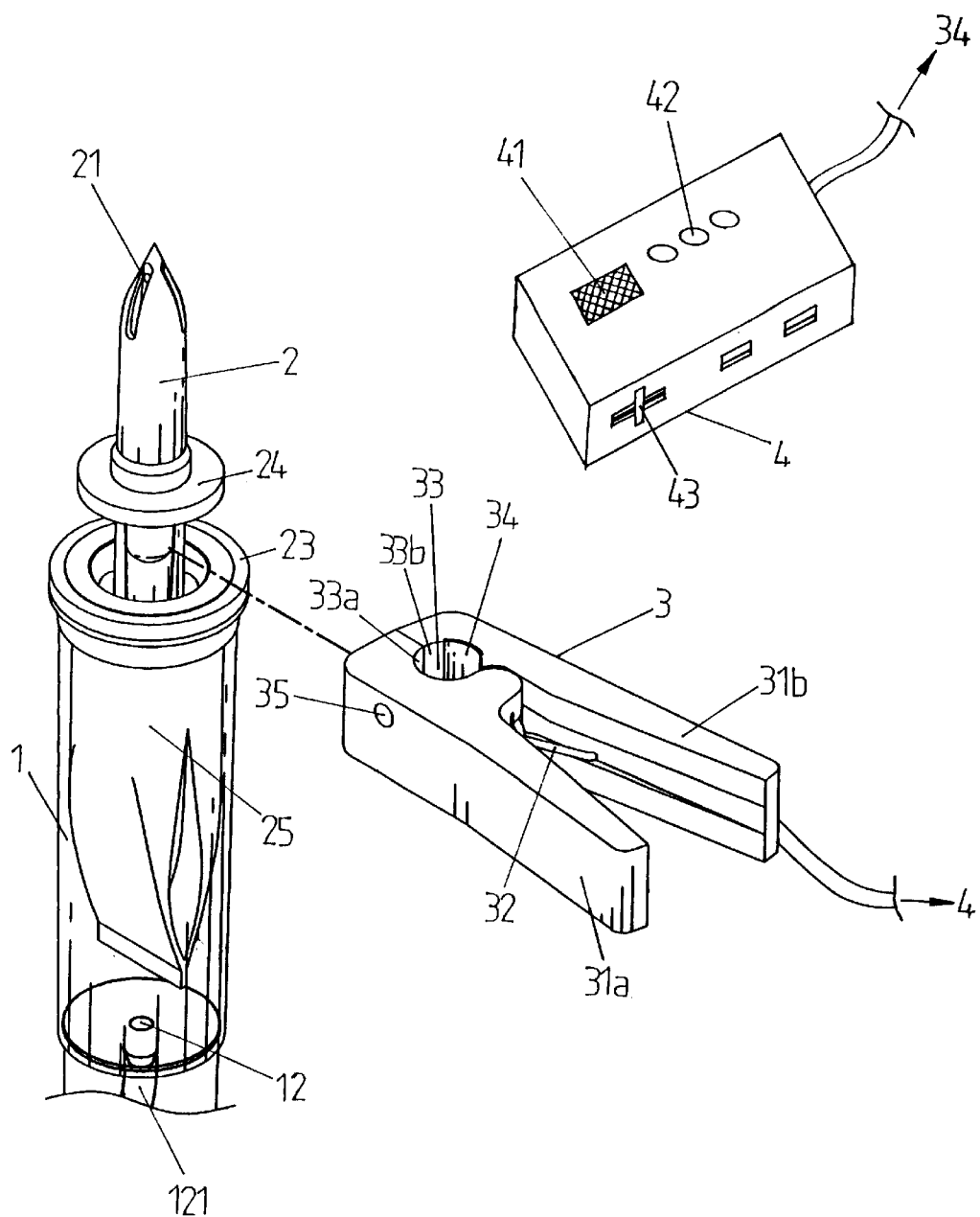
FIG. 2 is a partially assembled perspective view of the prewarning device of FIG. 1, showing a tubular needle has been connected to a throttling cylinder thereof.
Figure 3:
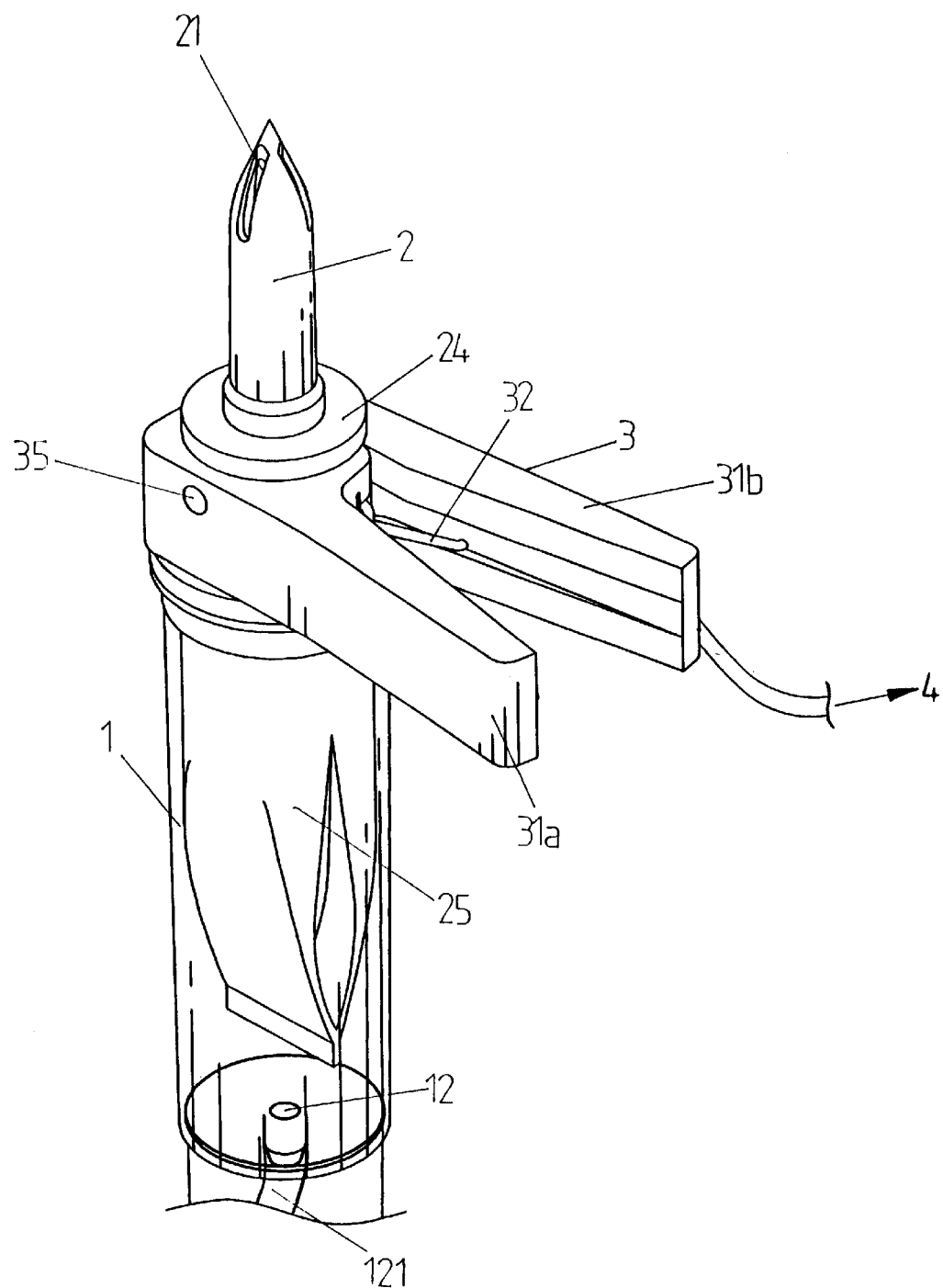
FIG. 3 shows a clamp of the prewarning device of FIG. 1 has been attached to a lower part of the tubular needle.

The tubular needle 2 is provided at a lower end with a disc portion 23 configured to securely fit into the open top 11 of the throttling cylinder 1, and a filtering bag 25 made of a web-like dense fabric connected to a lower periphery of the disc portion 23. When the tubular needle 2 is fitted in the top opening 11 of the throttling cylinder 1, the filtering bag 25 is located inside the throttling cylinder, as shown in FIG. 2, to serve as means for regulating the flow of a medical liquid to be transfused into a patient's vessel by way of instillation. A head portion of the tubular needle 2 opposite to the disc portion 23 and the filtering bag 25 is configured for inserting into a sealed mouth 52 of a bottle 5 containing a medical liquid 51 (see FIGS. 4 to 6). The head portion of the tubular needle 2 is forward tapered and lengthwise provided with a plurality of spaced slits 21, via which the medical liquid 51 contained in the bottle 5 flows into the tubular needle 2. The tubular needle defines a downward tapered inner space in which an oblong float 22 is disposed. When there is a sufficient amount of the medical liquid 51 flowing from the bottle 5 into the tubular needle 2 via the slits 21, the float 22 is always in a floating state and located at an upper position in the tubular needle 2. The tubular needle 2 is also provided around an outer wall at a position higher than the disc portion 23 by a predetermined distance with an annular stopper 24 adapted to press against the mouth 52 of the bottle 5 when the tubular needle 2 is inserted into the bottle 5 by a suitable depth. At least a portion of the tubular needle 2 between the disc portion 23 and the annular stopper 24 is transparent.

The clamp 3 includes a left handle 31a and a right handle 31b that have front claw ends and are pivotally connected to each other by means of a tension spring 32, such that the claw ends of the left and the right handles 31a, 31b are normally forced by the tension spring 32 to close to each other and define an opening 33 between them. The opening 33 is dimensioned for fitly clamping around the transparent portion of the tubular needle 2 between the disc portion 23 and the annular stopper 25 and is formed from two semicircular surfaces 33a, 33b that are inner wall surfaces of the claw ends of the handles 31a, 31b. A sensor 34 is attached to the semicircular surface 33b of the right handle 31b and electrically connected to the warning unit 4. A spot lamp 35 is set in the claw end of the left handle 31a opposite to the sensor 34, so as to project a light beam from the semicircular surface 33a toward the sensor 34.

The warning unit 4 is electrically connected to the sensor 34 via a wire and includes at least a buzzer 41 and a plurality of warning lights 42. The buzzer 41 could be actuated by a signal from the sensor 34 to emit warning sounds and cause a relevant warning light 42 to flash, so as to inform the patient's attendant family or a nurse when the medical liquid to be transfused is used up.

Figure 4:
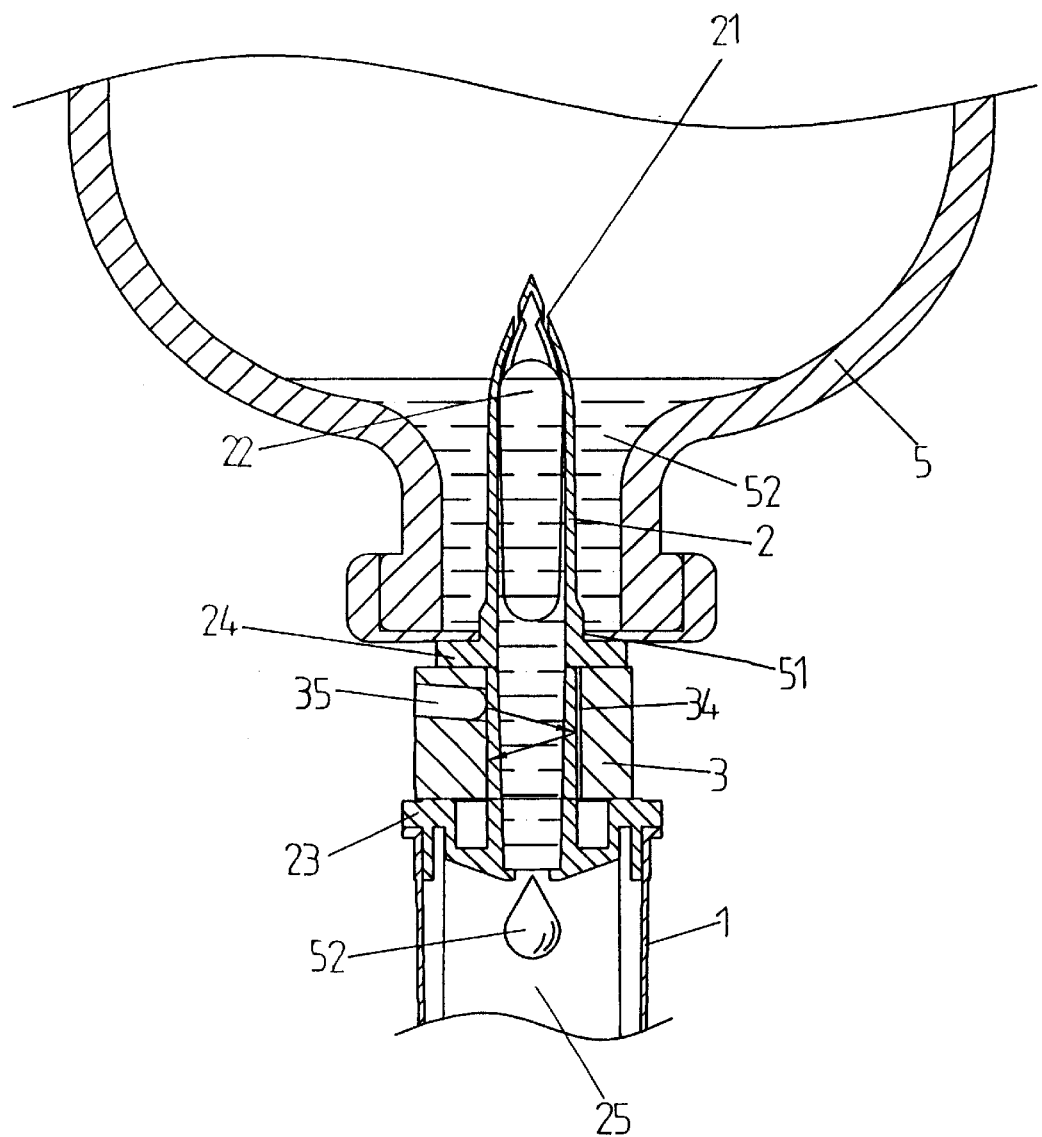
FIG. 4 shows a float is located at an uppermost position in the tubular needle above a sensor provided on the clamp attached to the tubular needle.

Please refer to FIG. 4. When the tapered head portion of the tubular needle 2 is inserted into the mouth 51 of the bottle 5 that is now turned upside down, the medical liquid 52 in the bottle 5 flows into the tubular needle 2 via the plurality of slits 21 at the head portion of the tubular needle and drops into the filtering bag 25 located in the throttling cylinder 1. The medical liquid 52 in the filtering bag 25 penetrates the bag and drops into the throttling cylinder 1 to flow to the duct 121 via the hole 12 on the closed bottom of the throttling cylinder 1 and finally reaches at the needle cannula connected to another end of the duct 121.

When the medical liquid 52 continuously flows through the tubular needle 2 to fill the same, the float 22 is kept in a floating state in the tubular needle 2, as shown in FIG. 4. As mentioned above, the tubular needle 2 is particularly configured to define a downward tapered inner space and an inner diameter of an upper part of the inner space is slightly larger than an outer diameter of the oblong float 22. This configuration prevents the float 22 floating in the tubular needle 2 from sealing the slits 21 and clogging the tubular needle 2, and therefore allows the medical liquid 52 to continuously flow into the tubular needle 2 via the slits 21. The spot lamp 35 on the clamp 3 clamped around the transparent portion of the tubular needle 2 between the disc portion 23 and the annular stopper 25 keeps projecting the light beam that passes through the medical liquid 52 and is received by the sensor 34, enabling the sensor 34 connected to the warning unit 4 to lighten a relevant warning light 42 on the warning unit 4, indicating the instillation of the medical liquid 52 is in a normal and safe condition.

Figure 5:
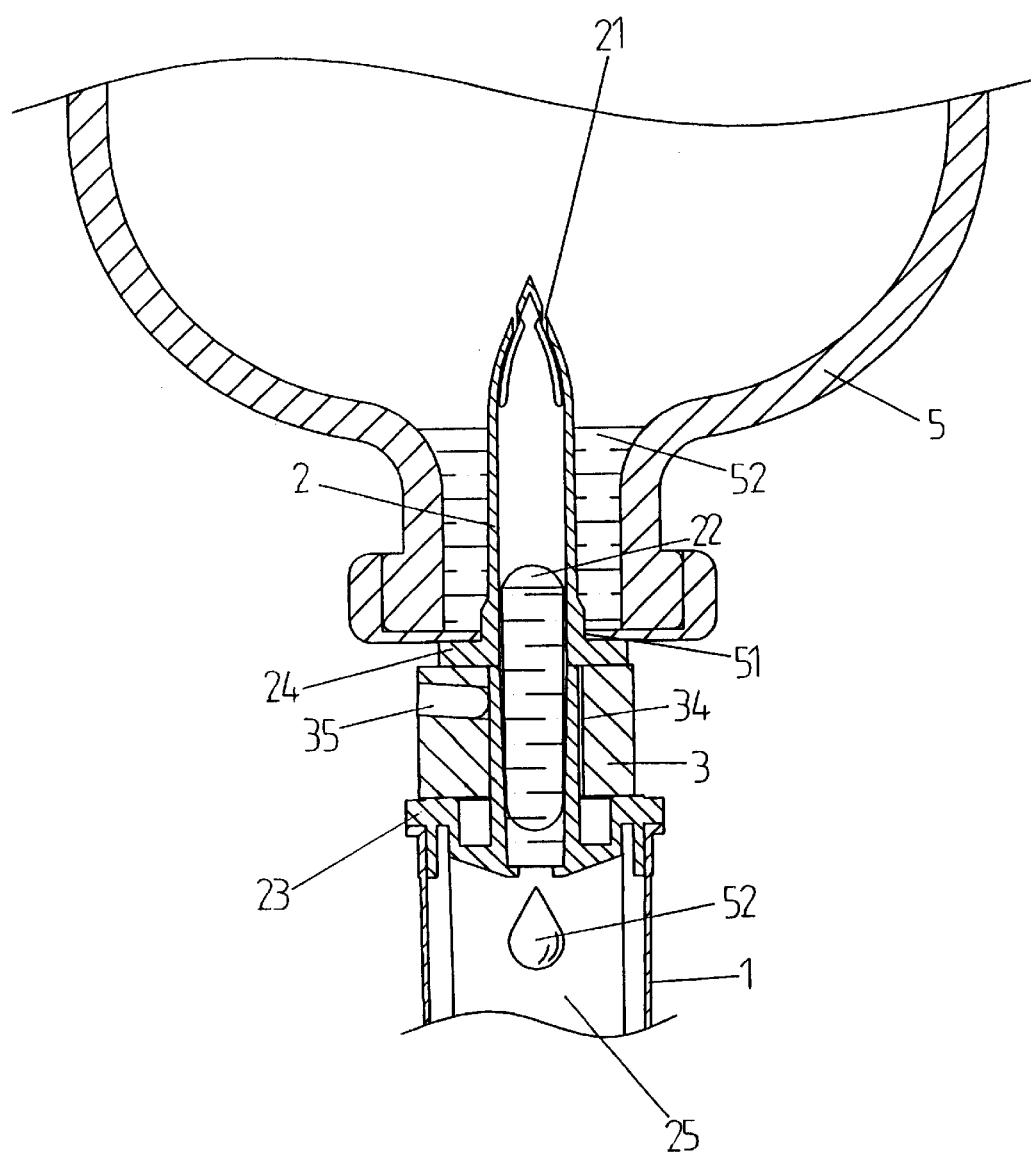
FIG. 5 shows the float in the tubular needle moves downward with the decreasing medical liquid being transfused to a patient by way of instillation to locate next to the sensor on the clamp.
Figure 6:
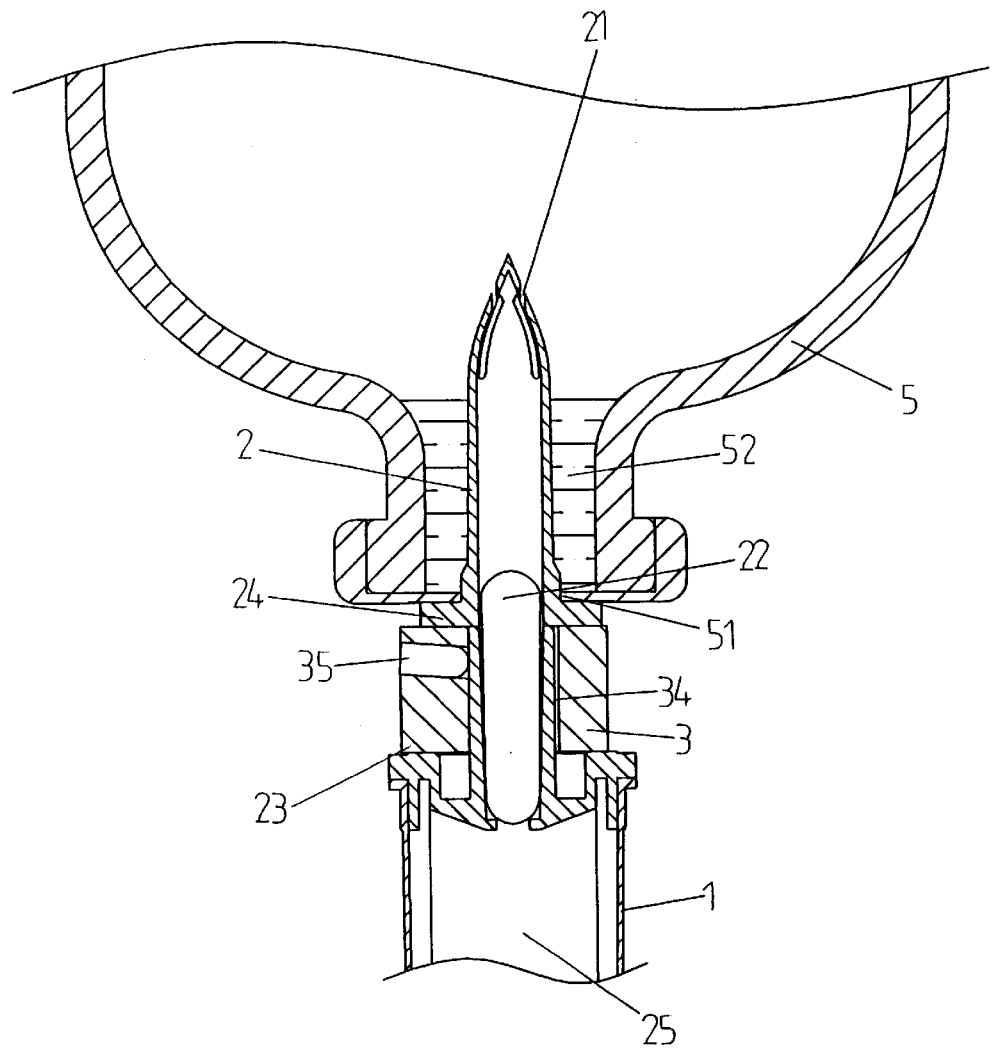
FIG. 6 shows the float in the tubular needle has moved downward to locate at a lowermost position in the tubular needle next to the sensor on the clamp.

Please further refer to FIGS. 5 and 6. When a level of the medical liquid 52 in the bottle 5 becomes lower than the slits 21 after the instillation has been done over a long time, the medical liquid 52 no longer flows from the bottle 5 into the tubular needle 2. Meanwhile, the medical liquid 52 already flown into the tubular needle 2 keeps dropping into the filtering bag 25 to gradually lower a level of the medical liquid 52 in the tubular needle 2 and cause the float 22 to move downward at the same time. Since the tubular needle 2 is configured to have a downward tapered inner space, the lowering float 22 would finally clog a narrower lower part of the tubular needle 2 when all the medical liquid 52 in the tubular needle 2 has dropped into the filtering bag 25, stopping any air from entering into the patient's vessel via the empty tubular needle 2 to endanger the patient.

When the float 22 clogs the lower part of the tubular needle 2, it also blocks the light beam emitted from the spot lamp 35. The sensor 34 that does not receive the light beam would immediately actuate the buzzer 41 on the warning unit 4 to emit warning sounds and cause another warning light 42 indicating an empty bottle 5 to flash, so that the patient's attendant family or the nurse is timely informed of the empty bottle 5 to replace the same with a new one. The warning unit 4 may also be additionally wired to a nursing station for the nursing attendants at a remote position to know the empty bottle 5 in a ward.

The following are some of the advantages of the prewarning device for instillation of medical liquid according to the present invention:

1. The device provides the function of stopping air from entering into the duct 121 and enables omission of conventional shutting means normally connected to the duct 121 for the same air-blocking purpose. This is achieved by way of fixedly connecting the tubular needle 2 to the throttling cylinder 1 and disposing the float 22 in the tubular needle 2 to control the flow of the medical liquid 52 and block any air.

2. The tubular needle 2 is fixedly connected to the throttling cylinder 1 to form an integral unit that could be more easily handled. A user needs only to hold the throttling cylinder 1 and insert the head portion of the tubular needle 2 into the mouth of the medical liquid bottle 5 to complete the preparatory work for instillation of the medical liquid.

An alternate form of the prewarning device of the present invention allows the device to be used with, for example, a blood transfusion bag that is not in the form of a typical bottle and contains light-impervious blood. In the alternate form of the prewarning device of the present invention, only the clamp 3 and the warning unit 4 are included, and the warning unit 4 is additionally provided with a selector switch 43. When the clamp 3 is clamped onto a transparent duct extended from the blood transfusion bag for delivering blood to a cannula, the selector switch 43 on the warning unit 4 is switched from a position corresponding to a normal instillation mode using the typical bottle 5 to a position corresponding to a blood transfusion mode using the blood transfusion bag. Since the blood is not impervious to light, the light beam emitted from the spot lamp 35 on the clamp 3 is not received by the sensor 34 and the buzzer 41 on the warning unit 4 is not actuated to sound. However, when the blood has been fully delivered from the blood transfusion bag and the duct becomes transparent again, the light beam emitted from the spot lamp 35 is directly projected onto the sensor 34 without being blocked by the blood. Thus, the buzzer 41 of the warning unit 4 is actuated by the sensor 34 to sound. In brief, the provision of the selector switch 43 allows the present invention to include only the clamp 3 and the warning unit 4 for use in transfusion of blood or other light-impervious fluid to prewarn an attendant family or a nurse of an empty blood transfusion bag.

The present invention has been described with a preferred embodiment thereof and it is understood that many changes and modifications in the described embodiment can be carried out without departing from the scope and the spirit of the invention that is intended to be limited only by the appended claims.

What is claimed is:

1. A prewarning device for instillation of medical liquid, comprising:

a throttling cylinder having a duct externally connected thereto;

a transparent tubular needle being fixedly connected to said throttling cylinder and provided at a forward tapered head portion with a plurality of spaced slits for inserting into a bottle containing a medical liquid to be transfused into a patient's vessel by way of instillation, and said tubular needle defining a downward tapered inner space in which a float is disposed;

a clamp having two front claw ends adapted to clamp around a lower part of said tubular needle, and a sensor provided at an inner surface of one of said two front claw ends; and a warning unit electrically connected to said sensor on said clamp; and said float gradually moving downward to a bottom of said tubular needle when the medical liquid in the bottle is used up in the instillation, and said sensor being able to sense said float at the bottom of said tubular needle and actuate said warning unit to emit a warning sound.

2. The prewarning device for instillation of medical liquid as claimed in claim 1, where in said throttling cylinder is a hollow cylindrical member having an open top and a closed bottom, and said duct being externally connected to a hole on said closed bottom.

3. The prewarning device for instillation of medical liquid as claimed in claim 1, wherein said tubular needle is connected to an open top of said throttling cylinder and includes an annular stopper provided at a position above said open top of said throttling cylinder by a predetermined distance, and said annular stopper being adapted to press against a mouth of said bottle after said tapered head portion of said tubular needle is inserted into said bottle.

4. The prewarning device for instillation of medical liquid as claimed in claim 1, wherein said clamp further includes a spot lamp set in the other one of said two front claw ends opposite to said sensor, so that light beam is normally projected from said spot lamp to said sensor.

5. The prewarning device for instillation for medical liquid as claimed in claim 1, wherein said warning unit includes a buzzer and a plurality of warning lights electrically connected to said sensor via a wire, and a selector switch for changing an actuating mode of said buzzer and said warning lights.

* * * * *